United States Patent
Slate et al.

(10) Patent No.: US 6,406,456 B1
(45) Date of Patent: Jun. 18, 2002

(54) JET INJECTOR

(75) Inventors: John B. Slate, San Diego; Michael W. Burk, San Marcos; Lanny A. Gorton, San Diego, all of CA (US)

(73) Assignee: Avant Drug Delivery Systems, Inc., San Diego, CA (US)

( * ) Notice: Subject to any disclaimer, the term of this patent is extended or adjusted under 35 U.S.C. 154(b) by 6 days.

(21) Appl. No.: 09/590,857

(22) Filed: Jun. 8, 2000

(51) Int. Cl.[7] ................................................ A61M 5/30
(52) U.S. Cl. .......................................... 604/68; 604/176
(58) Field of Search ............................... 604/68, 69, 70, 604/93.01, 118, 119, 140, 181, 115, 117, 134, 137, 187, 218, 197, 239, 240, 174, 176

(56) References Cited

U.S. PATENT DOCUMENTS

| | | | |
|---|---|---|---|
| 3,608,540 A | * | 9/1971 | Sartorius ..................... 600/563 |
| 4,421,508 A | * | 12/1983 | Cohen |
| 4,623,332 A | | 11/1986 | Lindmayer |
| 4,722,728 A | | 2/1988 | Dixon |
| 5,062,830 A | | 11/1991 | Dunlap |
| 5,116,313 A | | 5/1992 | McGregor |
| 5,312,335 A | * | 5/1994 | McKinnon |
| 5,399,163 A | | 3/1995 | Peterson |
| 5,480,381 A | | 1/1996 | Weston |
| 5,520,639 A | | 5/1996 | Peterson |
| 5,599,302 A | | 2/1997 | Lilley |
| 5,730,723 A | | 3/1998 | Castellano |
| 5,782,802 A | | 7/1998 | Landau |
| 5,891,086 A | | 4/1999 | Weston |
| 5,911,703 A | | 6/1999 | Slate |
| 5,957,886 A | | 9/1999 | Weston |
| 6,056,716 A | | 5/2000 | D'Antonio |

FOREIGN PATENT DOCUMENTS

| | | | | |
|---|---|---|---|---|
| EP | | 116961 A1 | * 12/2001 | ............ A61M/5/30 |
| WO | WO 94/23777 | | 10/1994 | |
| WO | WO 00/06228 | | 2/2000 | |
| WO | WO 01/87389 A1 | | * 11/2001 | ............ A61M/5/42 |

* cited by examiner

Primary Examiner—Brian L. Casler
Assistant Examiner—Catherine Serke
(74) Attorney, Agent, or Firm—Nydegger & Associates

(57) ABSTRACT

An injector for the intra-muscular, subcutaneous, or intra-dermal delivery of a fluid medicament to a patient includes a cylindrical member which has a closed end and an open end, and which is formed with a compartment between these two ends. An injection tube extends from the closed end through the cylindrical member and into the compartment. A suction pump is connected in fluid communication with the compartment to create a partial vacuum in the compartment when the open end of the cylindrical member is held against the skin of the patient. Due to this vacuum, skin of the patient is drawn into the compartment to position the tip of the injection tube against the skin. Also, skin that is adjacent the tip is drawn by the vacuum into the compartment. This stabilizes the skin around the injection tube tip and thereby minimizes any movement of skin relative to the tip during an injection of fluid medicament into the patient.

18 Claims, 5 Drawing Sheets

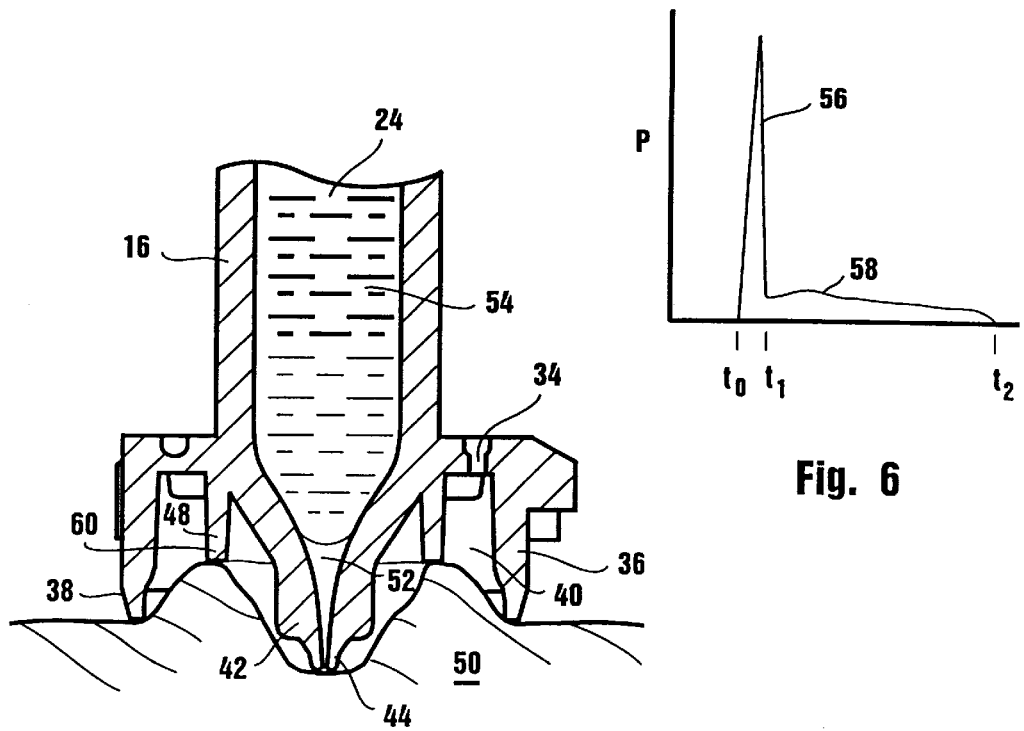
Fig. 5
Fig. 6
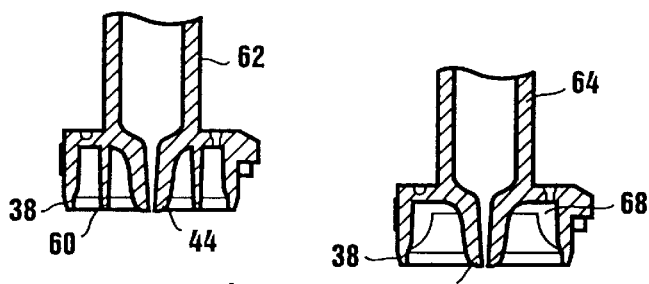
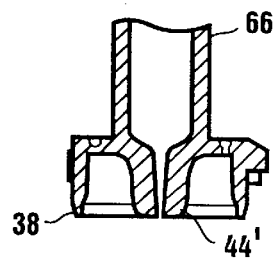
Fig. 7A'  Fig. 7B'  Fig. 7C'
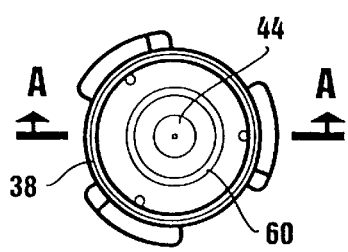
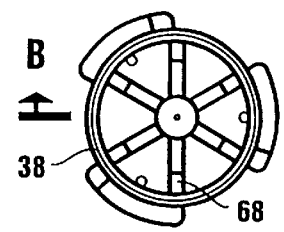
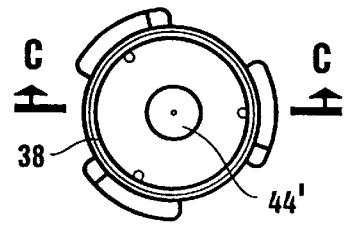
Fig. 7A  Fig. 7B  Fig. 7C

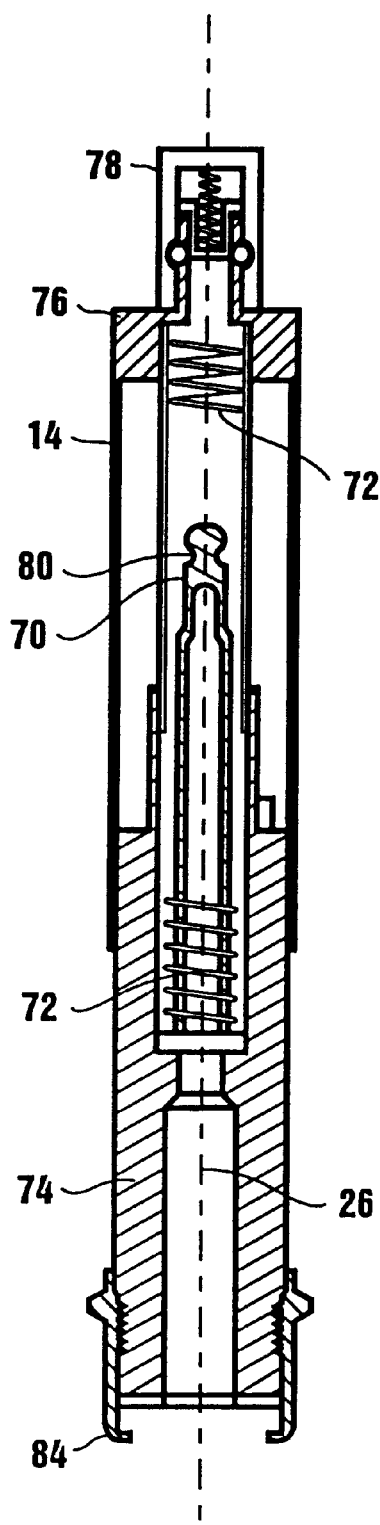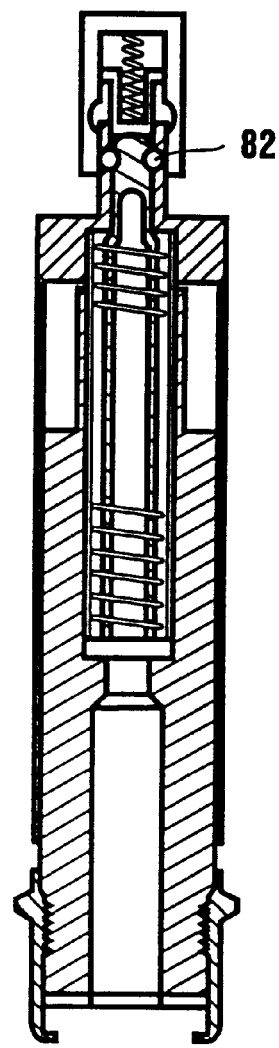
Fig. 8A
Fig. 8B

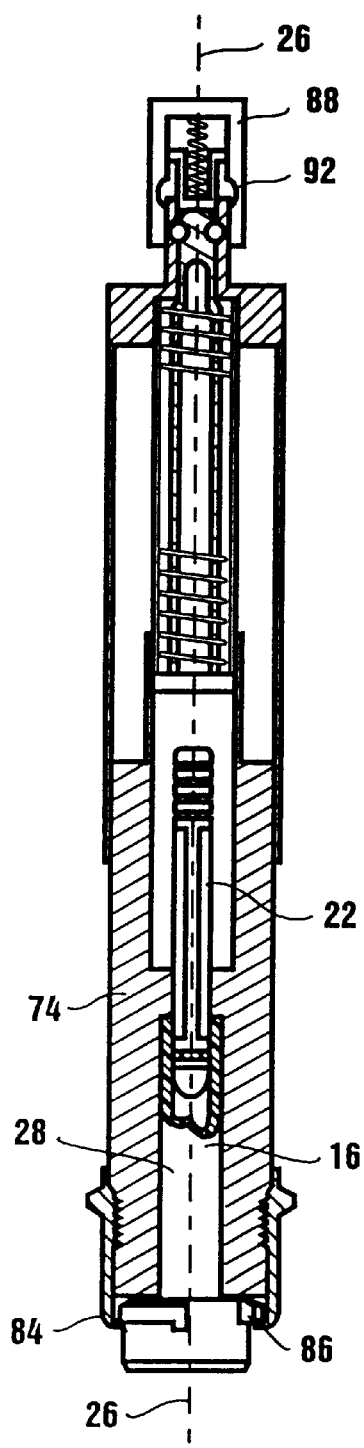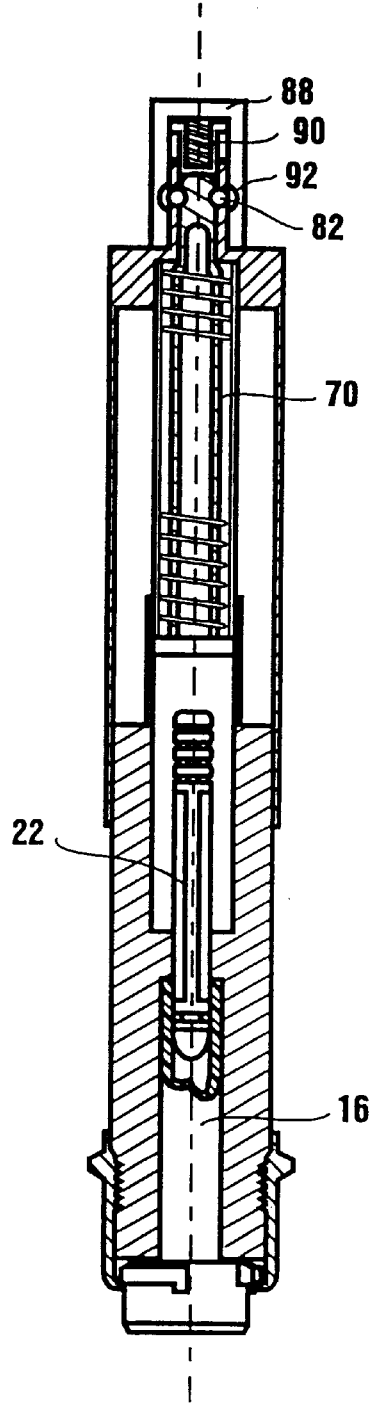
Fig. 8C
Fig. 8D

JET INJECTOR

FIELD OF THE INVENTION

The present invention pertains generally to injectors for subcutaneous delivery of a fluid medicament to a patient. More particularly, the present invention pertains to so-called needleless injectors. The present invention is particularly, but not exclusively, useful as an injector which will stabilize the tip of an injection tube against the skin of the patient to maintain a reliable skin-to-syringe relationship during an injection of fluid medicament.

BACKGROUND OF THE INVENTION

For many years, so-called needleless injectors have been commercially available for use in delivering fluid medicaments to a patient. The interest in this type of injector has been generated primarily for safety purposes because needleless injectors typically do not have the sharp projections which can accidentally or inadvertently cause unwanted cuts or punctures. More recently, the interest in needleless injectors has been heightened by the knowledge that many serious illnesses, such as AIDS, can be transmitted by needle punctures. Although otherwise desirable, the design of a needleless injector requires the balancing of often competing concerns which, if not properly handled, can make the result ineffective.

Because skin is elastic in nature, the interface that is established between the injection tube of a needleless injector/syringe and the skin of a patient during the injection of a fluid medicament is of extreme importance. Specifically, several interacting factors must be simultaneously considered. These factors include: seal pressure; holding force; skin stabilization; and tissue damage.

Seal pressure is important because a reliable skin-to-syringe relationship needs to be established which will prevent a leaking of the fluid medicament during an injection. Somewhat related to this concern for seal pressure is the necessity that there also be sufficient force for holding the syringe against the skin during an injection. Specifically, holding forces are important in that they prevent the syringe from coming off the skin due to hand movement of the operator or due to any momentum that may be generated during operation of the injector/syringe. In addition to the concerns regarding relative movement between the patient and the needleless injector/syringe, there is also an important concern for skin stabilization during an injection. Specifically, due to the elastic nature of skin, it is very important during the delivery of a fluid medicament that the injection tube not move off the hole that is created through the skin during the initial impulse. Finally, when collectively considering the above factors, it is a major design concern that tissue damage be absolutely minimized by eliminating sharp edges and projections on the injector/syringe which can cause skin damage and pain.

In order to address the syringe and skin interface concerns mentioned above, several important considerations for the structural design of an injector/syringe must be taken into account. One way by which a seal pressure can be established for the syringe interface with the skin is by suction. If suction is to be used for this purpose, it is necessary to create a suction (partial vacuum) compartment around the injection tube. It happens that both the seal pressure and the holding force will benefit from a larger suction compartment and a greater partial vacuum in the compartment. On the other hand, too large of a suction compartment, and too much suction in the suction compartment, will cause excessive skin distortion that can adversely affect skin stabilization. Further, too much suction (partial vacuum) force in the suction compartment can pull the skin too tight and cause the tip of the injection tube to press too hard against the skin. This, in turn, can lead to tissue damage such as subdermal hematomas (caused by the rupturing of capillaries) or bleeding (caused by an excessive puncturing of the skin beyond what is required for creating an injection hole in the skin). In summary, high sealing pressures and large holding forces can conflict with the desirable objectives of maximizing skin stabilization and minimizing tissue damage. Particularly, in the initial stages of an injection process when impact between the fluid medicament and the skin first occurs.

In order to initiate an injection process with a needleless injector it is obviously necessary to first create a "hole" in the skin through which a fluid medicament can be injected. It happens, however, that the creation of an appropriate hole in the skin requires that the initial discharge of fluid medicament be under considerable pressure. As a practical matter, the pressure that is necessary to create such a hole is much higher than the pressure that is subsequently required to inject the fluid medicament through the hole. Additionally, it happens that some injections need to be intra-muscular (e.g. some vaccinations), others need to be subcutaneous, (e.g. flu shots or insulin) while others are preferably intra-dermal (e.g. DNA vaccines and allergy testing). The point of all this is that, although seal pressure, holding force, skin stabilization and tissue damage are ever present concerns for needleless injectors, these factors are influenced by design consequences.

As mentioned above, in the manufacture of a needleless injector/syringe it is desirable to avoid the sharp edges and points which can cut, puncture, or otherwise compress tissue. On the other hand, it is also desirable that the tip of the injection tube through which the fluid medicament is delivered be small. One reason for this is that small tips are able to more effectively concentrate forces and establish fluid seals that are sufficient to prevent leaks than are large tips. This, of course, needs to be accomplished without causing tissue compression. Further, due to their more efficient fluid seals, small tips allow for the use of less fluid injection pressures and, thus, slower delivery times can be achieved. The result is a lower cost needleless injector/syringe that has thinner walls with less bulk and is, therefore, less cumbersome to use. In any event, this can not be achieved without properly balancing all of the other factors mentioned above, namely: seal pressure, holding force, skin stabilization and tissue damage.

In light of the above it is an object of the present invention to provide an injector for subcutaneous delivery of a fluid medicament to a patient which is able to slowly inject fluid medicament while avoiding tissue compression or damage. Another object of the present invention is to provide an injector for subcutaneous delivery of a fluid medicament to a patient which effectively stabilizes the skin against the injection tube of the injector during the delivery of the fluid medicament. Still another object of the present invention is to provide an injector for subcutaneous delivery of a fluid medicament to a patient which generates a sufficient seal pressure and a sufficient holding force to prevent the injector from coming off the patient during the delivery of the fluid medicament, and to thereby prevent unwanted lacerations and leaking of fluid medicament. Another object of the present invention is to provide a jet injector which can be configured for use in either intra-muscular, subcutaneous or intra-dermal injections. Still another object of the present invention is to provide a jet injector that has effective pressure variations for accomplishing both the creation of a "hole," and the subsequent injection of a fluid medicament through the hole. Yet another object of the present invention is to provide an injector for subcutaneous delivery of a fluid medicament to a patient which is simple to use, relatively easy to manufacture and comparatively cost effective.

SUMMARY OF THE PREFERRED EMBODIMENTS

In accordance with the present invention, an injector for subcutaneous delivery of a fluid medicament to a patient includes a substantially cylindrical shaped member that has a closed end and an open end. The closed end is defined by a surface, and this surface effectively functions as a base member for the injector. The sides of the cylindrical member are established by an outer wall which extends through a distance between the closed end and the open end. A compartment is thus established. Specifically, the compartment is bounded by the surface of the base member (i.e. the closed end of the cylindrical member), the outer wall which extends from the base member between the closed end and the open end, and the rim of the outer wall (i.e. the open end of the cylindrical member).

Inside the compartment of the injector, an injection tube extends outwardly toward the open end of the cylindrical member from the surface that defines the closed end of the member. Further, an inner wall also extends outwardly from the surface and into the compartment toward the open end. Thus, the compartment is separated into an outer compartment which is located between the outer wall and the inner wall, and an inner compartment that is located between the inner wall and the injection tube. Preferably, the outer wall, the inner wall and the injection tube are concentric. For intra-dermal (shallow) applications, the outer wall, inner wall and injection tube all extend through substantially the same distance from the surface at the closed end of the compartment. For intra-muscular or subcutaneous (deeper) applications, however, it is preferable for the injection tube to extend beyond the outer wall, and for the outer wall to extend beyond the inner wall.

The injector of the present invention also includes a suction means which is connected in fluid communication with both the inner compartment and the outer compartment. As intended for the present invention, when the open end of the cylindrical member (the rim of the wall) is held against the patient, the suction means is activated to draw skin into the compartments. By drawing skin into the compartments with this partial vacuum, the tip of the injection tube is positioned against the skin of the patient to establish an interface seal therewith. While the skin is thus held, it is stabilized to minimize any movement of skin relative to the tip of the injection tube during an injection of fluid medicament to the patient.

During an injection, the inner wall of the injector effectively acts as a skin suction depth control feature. For intra-muscular or subcutaneous injections, where the fluid is to be injected through the skin and respectively into muscle tissue or fat tissue, the inner wall is recessed from the outer wall and from the injection tube. The result in either case is an increased tension in the skin, and a consequent increase in the penetration depth of the injected fluid. Too much tension, however, can have adverse effects such as "skin creep," which results from the elastic nature of skin. The suction depth control features of the inner wall helps keep this tension within acceptable limits. For intra-dermal injections, where skin creep is not a major concern, the coextensive configuration of the outer wall, inner wall and injection tube will cause a comparative reduction in the tension in the skin, with a consequent decrease in the penetration depth of the injected fluid. Further, for shallower infusions (i.e. intra-dermal applications), it may be more effective if the suction remains on for ten to twenty seconds longer than would otherwise be used for intra-muscular applications.

Another aspect of the injector of the present invention is directed toward a configuration that will establish effective pressure variations during an injection. Specifically, for all applications it is desirable that the injector first create a "hole" in the skin, and that it then maintain a substantially steady infusion of medicament. As contemplated for the present invention, this can be accomplished by providing an air pocket in the distal portion of the injection tube. The effect of this air pocket will be to produce an initial pressure spike as fluid medicament is ejected from the injection tube. Due to this pressure spike, a "hole" is made through the skin. A normal infusion at lower pressures can then follow. It happens that, up to a point, the larger the air pocket in the distal portion of the injection tube, the deeper will be the penetration of the fluid medicament. Thus, intra-dermal (shallow) applications will most likely benefit from reductions in the size of the air pocket.

For an alternate embodiment of the present invention, the injector is configured to accept inserts that can be used to vary the skin suction depth control features mentioned above. These inserts can be configured in any of several ways. For example, they may have a plurality of inner walls to establish a respective plurality of annular suction compartments around the injection tube, or they can be configured with only the outer wall and a plurality of ribs which extend radially between the outer wall and the injection tube.

For the operation of the injector of the present invention, once the suction means has stabilized skin in the compartments, a drive means which is connected to the injection tube is activated. Upon activation of the drive means, fluid medicament is expelled through the injection tube to first create a hole in the skin, and to then inject the fluid medicament into the patient through the hole. As an example of an injection duty cycle, with the injector tip stabilized, the drive means may be activated for approximately one to five seconds for an injection of approximately one milliliter of fluid medicament.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 5 is a view of the needleless injector as seen in FIG. 3, with the injector filled with a fluid medicament;

FIG. 6 is a time plot of pressure variations in the fluid medicament during an injection;

FIG. 7A is a front end view of an alternate embodiment of the needleless injector that is suitable for use in intra-dermal applications;

FIG. 7A' is a cross sectional view of the needleless injector as seen along the line A—A in FIG. 7A;

FIG. 7B is a front end view of an alternate embodiment of the needleless injector that is suitable for use in intra-dermal applications;

FIG. 7B' is a cross sectional view of the needleless injector as seen along the line B—B in FIG. 7B;

FIG. 7C is a front end view of an alternate embodiment of the needleless injector that is suitable for use in intra-dermal applications;

FIG. 7C' is a cross sectional view of the needleless injector as seen along the line C—C in FIG. 7C;

FIG. 8A is an elevation cross sectional view of an actuator that is suitable for use with an injector of the present invention, with the actuator in a configuration prior to arming the actuator;

FIG. 8B is a view of the actuator of FIG. 8A in a cocking configuration;

FIG. 8C is a view of the actuator of FIG. 8A engaged with an injector of the present invention and with the trigger release mechanism being activated;

FIG. 8D is a view of the actuator of FIG. 8C configured for firing;

DESCRIPTION OF THE PREFERRED EMBODIMENT

Figure 1:
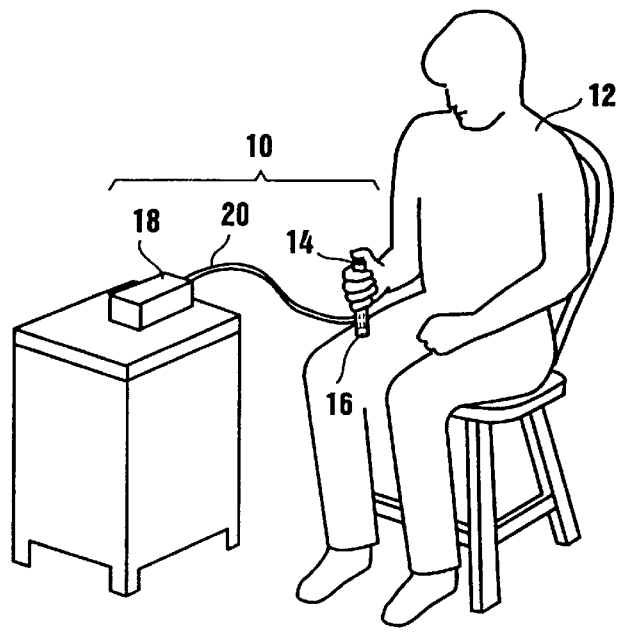
FIG. 1 is a perspective view of a patient using a device with a needleless injector of the present invention.

Referring initially to FIG. 1, a system for delivering a fluid medicament in accordance with the present invention is shown and is generally designated 10. For the purposes of the present invention, the system 10 is used to deliver a fluid medicament to a patient 12 by selectively injecting the fluid medicament either into a muscle (intra-muscular), subcutaneous, or into the skin (intra-dermal). For all modes of operation, the system 10 essentially includes an injector 14 which is engageable with a needleless syringe 16. When so engaged, the injector 14 is used to activate the needleless syringe 16, and thereby expel the fluid medicament from the syringe 16. To stabilize and hold the syringe 16 against the skin of the patient 12 during an injection, the system 10 includes a suction pump 18 which is connected in fluid communication with the syringe 16 via a vacuum line 20. More specifically, the generation of a partial vacuum between the syringe 16 and the skin of the patient 12 accomplishes at least three functions. First, the partial vacuum forms the skin with a desired tension for the injection. It should be noted that the desired tension for an intra-muscular injection is different than the tension for an intra-dermal injection. Second, as stated above, the partial vacuum helps stabilize and hold the syringe 16 against the patient 12. And third, the partial vacuum generates a fluid seal between the syringe 16 and the patient 12 that allows for the effective delivery or injection of a fluid medicament 54.

Figure 2:
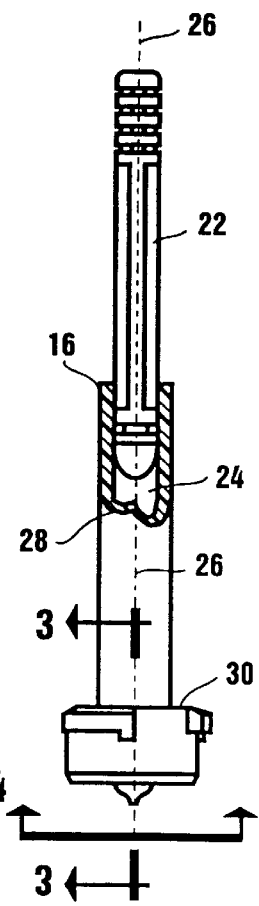
FIG. 2 is an elevation view of an assembled needleless injector according to the present invention with portions broken away for clarity.
Figure 3:
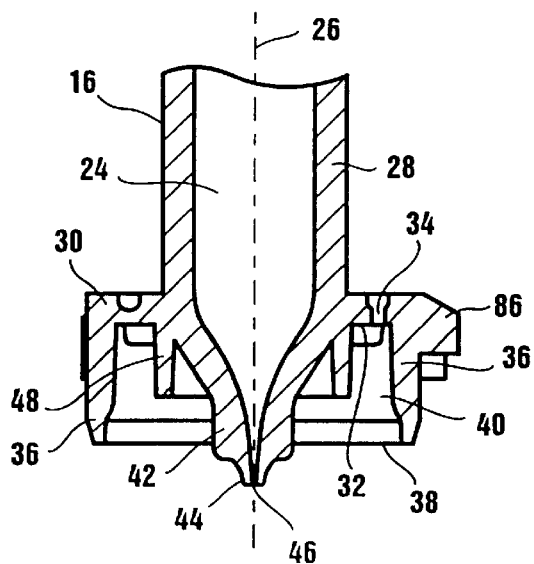
FIG. 3 is a cross sectional view of the needleless injector as seen along the line 3—3 in FIG. 2.
Figure 4:
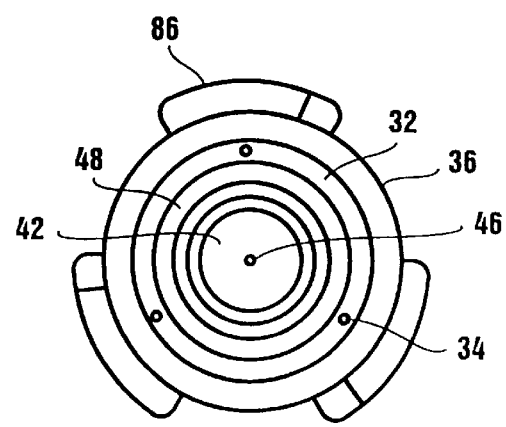
FIG. 4 is a front end view of the needleless injector as seen along the line 4—4 in FIG. 2.
Figure 8E:
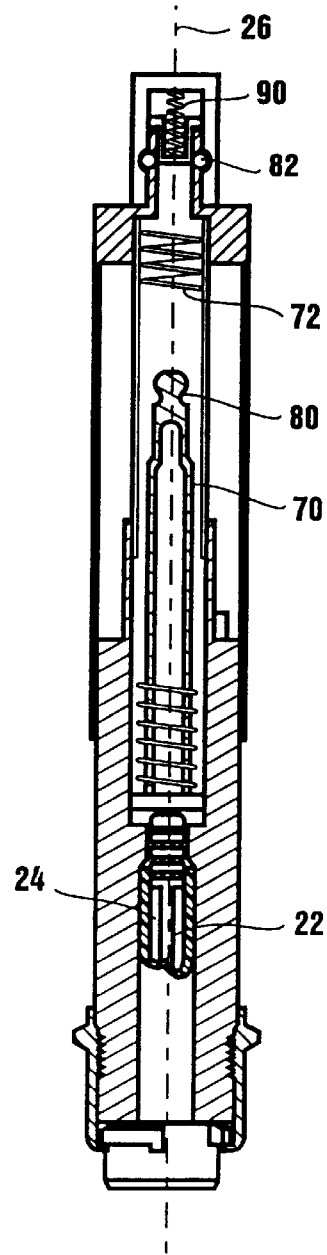
FIG. 8E is a view of the actuator of FIG. 8C in a configuration after a firing sequence.

In detail, a preferred embodiment for the syringe 16 of the present invention can be best appreciated by cross referencing FIGS. 2, 3 and 4. In FIG. 2 it will be seen that the syringe 16 includes a plunger 22. Specifically, as shown in FIG. 2, the plunger 22 is positioned to be advanced into a fluid chamber 24 along a central axis 26. As shown, the central axis 26 is effectively the longitudinal axis of the cylindrical barrel 28 that defines the fluid chamber 24.

At the distal end of the barrel 28 and fluid chamber 24, the syringe 16 is formed with a base member 30 which has a surface 32 that faces in a distal direction from the fluid chamber 24. As shown in FIGS. 3 and 4, the base member 30 is formed with at least one aperture 34 that extends through the base member 30 to the surface 32. Also, the base member 30 is formed with a cylindrical shaped skirt 36 that extends distally (outwardly) from the surface 32. More specifically, the skirt 36 has a circular shaped rim 38 which is centered on the central axis 26, and which helps to define a compartment 40. For purposes of the present invention, the compartment 40 of the syringe 16 is generally defined as the space that is enclosed between the surface 32 of base member 30, the skirt 36 that extends from the surface 32, and the plane in which the rim 38 lies. Stated differently, the compartment 40 is bounded by a closed end (surface 32), the skirt 36, and an open end (defined by rim 38).

Still referring to FIG. 3 it will be seen that an injection tube 42 extends distally from both the fluid chamber 24 and the surface 32 of base member 30. Further, the injection tube 42 is formed with a tip 44 that is formed with a generally circular shaped port 46. Preferably, the ratio of the diameter of the circular rim 38 to the diameter of the circular port 46 of injection tube 42 is approximately sixteen to one (16:1). Also, as shown in FIG. 3, the syringe 16 includes an abutment 48 which is generally cylindrical in shape and which extends distally (outwardly) from the surface 32. As shown, the abutment 48 is located within the compartment 40 between the skirt 36 and the injection tube 42. Preferably, both the abutment 48 and the skirt 36 are co-axially oriented relative to the central axis 26. For an embodiment of the present invention wherein it is desired to effect intra-dermal injections (i.e. into the skin), the tip 44 of the injection tube 42, the rim 38 of skirt 36, and the abutment 48 will all extend from the surface 32 through substantially the same distance. On the other hand, for an embodiment of the present invention wherein it is desired to effect intra-muscular injections, these components will extend distally through different distances. Specifically, the tip 44 will extend distally beyond the rim 38 of skirt 36, and the rim 38 of skirt 36 will extend distally beyond the abutment 48. The consequence of this configuration (intra-muscular) is best appreciated with reference to FIG. 5.

When viewing FIG. 5, it is to be appreciated that the skin 50 of patient 12 is shown as if the syringe 16 is engaged with an activated suction pump 18. Specifically, with such engagement the vacuum line 20 is placed in fluid communication with the compartment 40 via the aperture 34. Consequently, a partial vacuum in a range of around six to twelve inches of mercury (6–12 inHg) can be created inside the compartment 40. Due to this partial vacuum, the skin 50 is partially drawn into the compartment 40. Specifically, as shown, the skin 50 is drawn into the compartment 40 until it comes into contact with the abutment 48. Importantly, this places the skin 50 into a state of tension at the point where the tip 44 of the injection tube 42 is positioned against the skin 50.

FIG. 5 also indicates that, prior to an injection, an air pocket 52 can be formed in the injection tube 42 between the tip 44 of the injection tube 42 and the fluid medicament 54 in fluid chamber 24. For the present invention, this air pocket 52 can be formed in any manner well known in the art, and it can be of any desired volume. The importance of the air pocket 52 is, perhaps, best appreciated by reference to FIG. 6.

In FIG. 6 it is to be appreciated that at a time, to, when the system 10 is first activated to effect an injection, the fluid medicament 54 will be accelerated through the injection tube 42. Due to the presence of an air pocket 52, the initial acceleration of the fluid medicament 54 through the injection tube 42 will be relatively rapid. The result of this rapid acceleration is a pressure spike 56 in the fluid medicament in the time interval between $t_0$ and $t_1$, (see FIG. 6) which effectively causes the initially expelled fluid medicament 54 to create a hole in the skin 50. The duration of the time interval between $t_0$ and $t_1$ will, in most cases, be about one millisecond (1 ms). It happens that there will be a limit to the effective size of the air pocket 52. Beyond this limit, the magnitude of the pressure spike 56 will plateau and, perhaps, even decrease. Once a hole has been created, and there is no longer an air pocket 52 in the injection tube 42, infusion of any fluid medicament 54 that is remaining in the fluid chamber 24 will be accomplished at a reduced infusion pressure 58. As shown in FIG. 6, the infusion pressure 58 will be substantially maintained through the time interval from $t_1$ to $t_2$. Depending on the volume of fluid medicament 54 that is to be infused, the time interval from $t_1$ to $t_2$ will be generally in the range of one to five seconds and, in the case of an intra-dermal injection, can be as much as twenty seconds in duration. It will be appreciated by the skilled artisan, however, that the magnitudes of the pressure spike 56 and the infusion pressure 58, as well as the duration of the infusion are variables which can be controlled by the operator in ways well known in the pertinent art.

As indicated above, the system 10 of the present invention is directed toward both intra-muscular and intra-dermal applications. As also indicated above, the relation between the rim 38 of skirt 36, the abutment 48 and the tip 44 of the injection tube 42 is somewhat dependent on the application. For intra-dermal applications, it is preferable that the rim 38 of skirt 36, the forward edge 60 of abutment 48 and the tip 44 of the injection tube 42 all lie substantially in the same plane.

FIGS. 7A, 7B and 7C respectively show various configurations for syringes that can be used for intra-dermal applications. Specifically, FIG. 7A shows an syringe 62 wherein the rim 38 of skirt 36, the forward edge 60 of abutment 48 and the tip 44 of the injection tube 42 all lie substantially in the same plane. FIGS. 7B and 7C respectively show syringes 64 and 66 wherein this configuration is somewhat modified by replacing the abutment 48 With a plurality of extensions 68 (FIG. 7B), and by removing the abutment 48 entirely and, instead, providing a blunter tip 44' (FIG. 7C). In all of these embodiments, however, the rim 38 of skirt 36 and the tip 44 (tip 44') lie in substantially the same plane.

Activation of the system 10 is best appreciated by cross referencing FIGS. 8A, 8B, 8C, 8D and 8E. First, in FIG. 8A, it will be seen that the injector 14 includes a drive bar 70 which is influenced by a drive spring 72. More specifically, the drive spring 72 is positioned between a slide member 74 and a base member 76. With this combination of components, the injector 14 can be armed simply by moving the slide member 74 toward the base member 76 to compress the drive spring 72 therebetween. In addition to compressing the drive spring 72, this action also engages the drive bar 70 with the release mechanism 78. In detail, as the drive bar 70 is moved toward the release mechanism 78, the indents 80 that are formed at the proximal end of the drive bar 70 become engaged with the ball bearings 82 (see FIG. 8B). Thus, the drive bar 70 is held in its firing (cocked) position.

As shown in FIG. 8C, once the drive bar 70 has been cocked, the syringe 16 can be engaged with the injector 14. This is done by engaging the grip 84 on the injector 14 with the ears 86 that are formed on the syringe 16. This engagement also aligns the plunger 22 of syringe 16 with the drive bar 70 of the injector 14. For reference purposes, this alignment will be substantially along the central axis 26.

In order to fire the injector 14, it is necessary to depress the firing cap 88 from a position as shown in FIG. 8C to the position shown in FIG. 8D. This does two things. First, by depressing the firing cap 88 the firing spring assembly 90, which is mounted inside the firing cap 88, is compressed. Second, depression of the firing cap 88 causes the ball bearings 82 to align with the recesses 92 that are formed into the firing cap 88. The result of all this is that the compressed firing spring assembly 90 urges against the drive bar 70 to move the drive bar 70 in a distal direction along the central axis 26. This action, in turn, moves the ball bearings 82 into the recesses 92. At this point, the drive bar 70 is released from the grip of the ball bearings 82 and the drive spring 72 is allowed to elongate. The drive spring 72 then forces the drive bar 70 into contact with the plunger 22.

In accordance with the above disclosure, as the plunger 22 is advanced through the fluid chamber 24 any air pocket 52 in the injection tube 42 will cause a pressure spike 56. Recall, this pressure spike 56 facilitates the creation of a hole in the skin 50 of the patient 12. Subsequently, the drive spring 72 will act on the drive bar 70 and plunger 22 to effect an infusion pressure 58.

Figure 9:
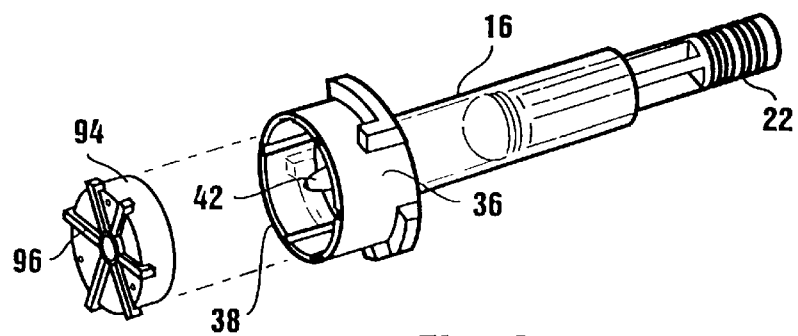
FIG. 9 is an exploded view of an alternate embodiment for an injector incorporating an insert.

For an alternate embodiment of the system 10 of the present invention, the syringe 16 is provided with an insert 94. Specifically, the insert 94 can be configured with any abutment 96 that is appropriate for the desired use of the system 10. As shown in FIG. 9, the abutment 96 comprises a plurality of radially oriented ribs. Other forms of the abutment 96 may be used and, the abutment can be dimensioned to accommodate either intra-muscular or intra-dermal applications.

While the particular Jet Injector as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An injector for delivering a fluid medicament to a patient which comprises:

a base member having a surface;

a skirt having a rim, said skirt extending outwardly from said surface to position said rim thereof at a distance from said surface, said skirt and said surface of said base member defining a compartment therebetween;

an injection tube having a tip extending outwardly from said surface and through said compartment for injecting the fluid medicament into the patient;

an abutment projecting from said surface of said base member and into said compartment between said skirt and said injection tube; and a suction means in fluid communication with said compartment through said surface of said base member for creating a partial vacuum in said compartment when said rim of said skirt is held against the patient, said suction means drawing skin into contact with said abutment to urge said tip of said injection tube against the skin of the patient to establish an interface seal therebetween, and to stabilize skin adjacent said tip, against said tip, to minimize movement of skin relative to said tip during an injection of fluid medicament.

2. The injector as recited in claim 1 wherein said skirt is formed as an annulus.

3. The injector as recited in claim 2 wherein said skirt and said abutment are substantially cylindrical in shape and wherein said skirt, said abutment and said injection tube are substantially concentric.

4. The injector as recited in claim 1 wherein said tip of said injection tube extends beyond said rim of said skirt, and said rim of said skirt extends beyond said abutment, and wherein, for an intra-muscular injection of the fluid medicament, said abutment limits the drawing of skin into said compartment to a depth of about one tenth of an inch (0.10 in) past said tip of said injection tube.

5. The injector as recited in claim 1 wherein said rim of said skirt, said abutment and said tip of said injection tube are all at a substantially same distance from said surface.

6. The injector as recited in claim 1 further comprising a drive means connected to said injection tube for expelling fluid medicament through said injection tube during an injection of fluid medicament.

7. The injector as recited in claim 6 further comprising a means for creating an air pocket in said injection tube between said tip of said injection tube and a fluid medicament being held in said injector, said air pocket being located immediately proximal said tip.

8. The injector as recited in claim 6 wherein said drive means is activated for approximately one to five seconds for an injection of approximately one milliliter of fluid medicament.

9. The injector as recited in claim 1 wherein said skirt is formed as a cylinder having a diameter, and wherein said injection tube is formed with a fluid injection channel having a diameter, and further wherein the ratio of said cylinder diameter to said fluid injection channel diameter is approximately sixteen to one (16:1).

10. The injector as recited in claim 1 wherein said base, said skirt, said abutment and said injection tube are made of a medical grade plastic.

11. The injector as recited in claim 1 wherein said abutment is formed as an insert, said insert being selectively positioned in said compartment between said skirt and said injection tube.

12. An injector for delivering a fluid medicament to a patient which comprises:
a hollow substantially cylindrical member defining a central axis and having a closed end and an open end and formed with a compartment between said closed end and said open end;
an injection tube having a tip extending along said central axis from said closed end;
suction means in fluid communication with said compartment for creating a partial vacuum therein when said open end of said cylindrical member is held against the patient, said vacuum drawing the skin of the patient into said compartment to position said tip of said injection tube against the skin and to stabilize skin adjacent said tip against movement of skin relative to said tip during injection of fluid medicament through said tube;
an abutment extending from said closed end into said compartment between said cylindrical member and said injection tube to limit the drawing of skin into said compartment; and
a drive means connected to said injection tube for expelling fluid medicament through said injection tube during an injection of fluid medicament.

13. The injector as recited in claim 1 wherein said cylindrical member is formed with a rim surrounding said open end of said cylindrical member, and further wherein said tip of said injection tube extends from said closed end beyond said rim of said cylindrical member, and said rim of said cylindrical member extends from said closed end beyond said abutment.

14. The injector as recited in claim 1 wherein said cylindrical member, said abutment, and said injection tube extend from said closed end through approximately a same said distance.

15. The injector as recited in claim 1 wherein said abutment comprises a plurality of ribs, each said rib extending from said closed end and oriented radially between said injection tube and said cylindrical member.

16. The injector as recited in claim 12 wherein said drive means is activated for approximately one to five seconds for an injection of approximately one milliliter of fluid medicament and wherein said partial vacuum is in a range of approximately six to twelve inches of mercury (6–12 in Hg) and draws skin into said compartments to a depth of approximately one tenth of an inch (0.10 in).

17. A method for delivering a medical medicament to a patient which includes the steps of:
positioning an injector against the skin of the patient, said injector including a hollow substantially cylindrical member having a closed end and an open end and formed with a compartment therebetween, an injection tube having a tip extending from said closed end, a suction means in fluid communication with said compartment, an abutment extending from said closed end into said compartment between said cylindrical member and said injection tube, and a drive means connected with said injection tube for injecting fluid medicament therethrough;
holding said open end of said cylindrical member against the patient;
activating said suction means to create a partial vacuum in said compartment, said vacuum drawing the skin of the patient into the compartment and against said abutment to position said tip of said injection tube against the skin and to stabilize skin against movement thereof relative to said tip during injection of fluid medicament through said tube; and
activating said drive means to expel fluid medicament through said injection tube for subcutaneous delivery of fluid medicament to the patient.

18. The method as recited in claim 17 further comprising the step of creating an air pocket in said injection tube between said tip of said injection tube and a fluid medicament being held in said injector, said air pocket being located immediately proximal said tip.

* * * * *

UNITED STATES PATENT AND TRADEMARK OFFICE
CERTIFICATE OF CORRECTION

PATENT NO. : 6,406,456 B1
DATED : June 18, 2001
INVENTOR(S) : John B. Slate, Michael W. Burk and Lanny A. Gorton It is certified that error appears in the above-identified patent and that said Letters Patent is hereby corrected as shown below:

<u>Column 7,</u>
Line 1, delete "to" insert -- $t_o$ --
Line 46, delete "with" insert -- with --

<u>Column 10,</u>
Line 8, delete "1" insert -- 12 --
Line 15, delete "1" insert -- 12 --
Line 18, delete "said"
Line 19, delete "1" insert -- 12 --

Signed and Sealed this

Twenty-second Day of October, 2002

*Attest:*

JAMES E. ROGAN
*Attesting Officer*     *Director of the United States Patent and Trademark Office*